United States Patent [19]

Ridgeway

[11] Patent Number: 4,487,580
[45] Date of Patent: Dec. 11, 1984

[54] ORTHODONTIC BRACKET HOLDER

[76] Inventor: William V. Ridgeway, 3245 E. 1st St., Long Beach, Calif. 90803

[21] Appl. No.: 583,015

[22] Filed: Feb. 23, 1984

[51] Int. Cl.³ .............................................. A61C 7/00
[52] U.S. Cl. ...................................................... 433/3
[58] Field of Search ........................................... 433/3

[56]  References Cited
U.S. PATENT DOCUMENTS 3,686,762  8/1972  Sutter ...................................... 433/3
4,035,919  7/1977  Cuszto .................................... 433/3

Primary Examiner—Robert Peshock
Attorney, Agent, or Firm—William C. Babcock

[57] ABSTRACT

A spring loaded holder that includes a pair of rigid bodies that are laterally movable, which bodies define adjacent end surfaces of arcuate convex shape that may removably and frictionally grip concave end edges of gingival occlusal wings that are disposed outwardly from the base of an orthodontic bracket. When the bracket is so gripped it may be moved to a position where the surface of the base most remote from the holder may be bonded to a tooth. To prevent inadvertent rotation of the orthodontic bracket when so gripped relative to the holder, at least one of the pair of bodies includes an elongate protuberance that engage an anchor wire receiving groove in the surface of the bracket most distant from the base. The bodies if desired may be formed as an integral part of the holder.

4 Claims, 6 Drawing Figures

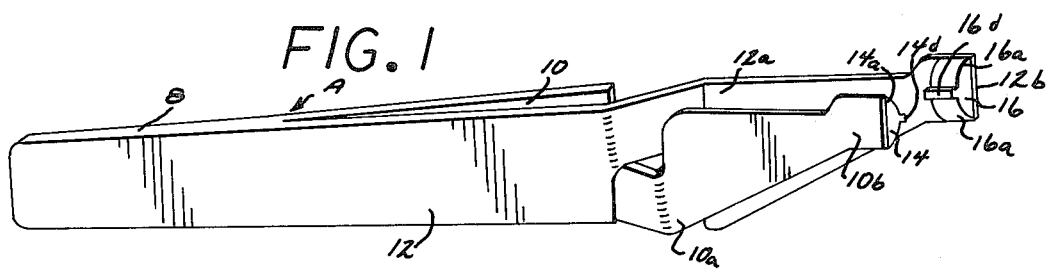
FIG. 1
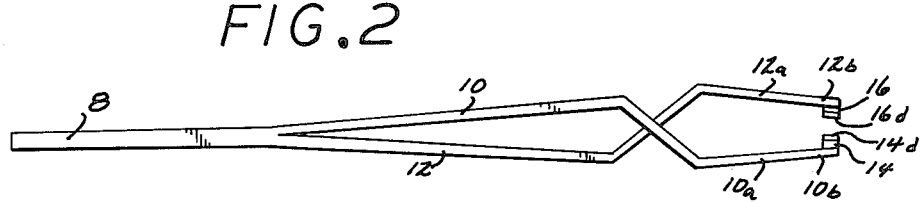
FIG. 2
FIG. 3  FIG. 4  FIG. 5
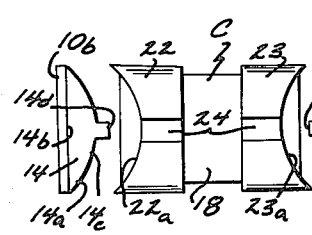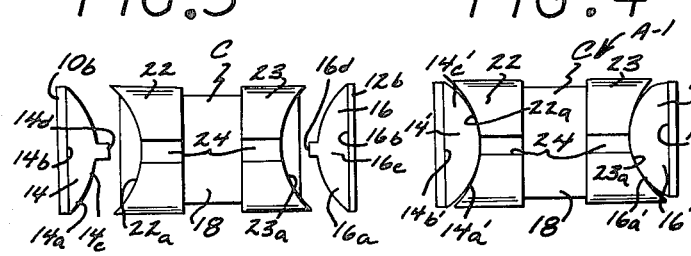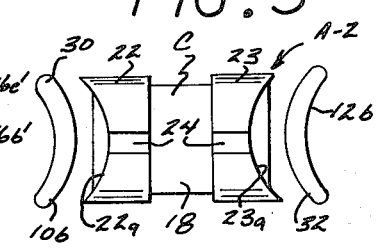
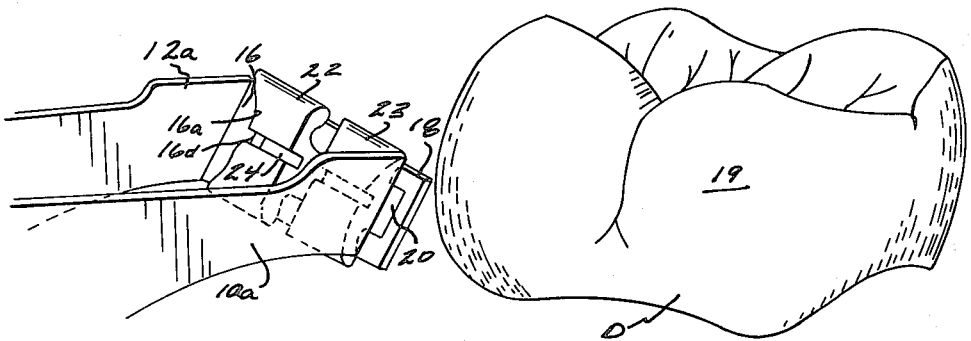
FIG. 6

ORTHODONTIC BRACKET HOLDER

DESCRIPTION OF THE PRIOR ART

Orthodontic brackets are commercially available that have gingival occlusal wings that are disposed outwardly from the base of the bracket. The opposed end edges of the wings are concave and curve towards one another. The wings as is common with orthodontic brackets have anchor wire engaging grooves defined therein.

The brackets due to their small size and the concave end edges of the wings are difficult to removably hold and manipulate in positioning the bases of the brackets relative to desired portions of teeth to which they will be removably secured by a suitable bonding agent.

A major object of the present invention is to provide a holder for removably gripping the concave end edge of the wings in a firm manner to permit the quick and easy positioning of the orthodontic brackets to have the bases of the brackets bonded thereto.

A further object of the invention is to supply a holder that not only grips the opposed concave end edges of the wings on a bracket, but also includes an elongate rigid means that removably engage the anchor wire receiving groove to prevent inadvertent rotation of the bracket when so gripped.

A still further object of the invention is to provide a forceps like instrument that includes two wing engaging portions that may be either integral portions of the orthodontic bracket holder or separate bodies that are secured thereto.

These and other objects and advantages of the invention will become apparent from the following description thereof.

BRIEF DESCRIPTION OF THE DRAWINGS

FIG. 1 is a perspective view of spring loaded forceps that include a pair of movable bodies capable of removably engaging opposed concave end edges on the wing defining portion of an orthodontic bracket, as well as an anchor wire receiving groove, to permit movement of the bracket to a position where it may be bonded to a tooth;

FIG. 2 is a top plan view of the orthodontic bracket holder shown in FIG. 1;

FIG. 3 is an end elevational view of the orthodontic bracket holder illustrating the two bodies that removably engage the two concave end edges as well as the anchor wire receiving groove;

FIG. 4 is an end elevational view of the orthodontic bracket holder illustrating the two bodies, but with the bodies capable of gripping only the opposed concave end edges;

FIG. 5 is an end elevational view of the forceps with the two movable bracket engaging bodies being formed as an integral part of the forceps; and FIG. 6 is a perspective view of a portion of the holder gripping an orthodontic bracket and the holder moving the bracket towards a tooth to be bonded to the latter,

SUMMARY OF THE INVENTION

The present invention is an orthodontic bracket holder that is adapted for use on brackets of the type in which the wings that are disposed outwardly from the bases have end edges that are concave and curve towards one another.

The present invention includes a forceps like instrument that has two elongate arms that are so spring loaded that the free end portions of the arms tend to at all times to move into pressure contact with one another. The invention includes two rigid bodies secured to the adjacent surfaces of the end portions, or if desired the bodies may be formed integral with the end portions.

The two bodies define adjacent end surfaces of convex shape that may removably engage the two concave end edges of a bracket and frictionally grip the end edges to permit the bracket to be moved to a position where the base thereof may be bonded to a tooth. In a preferred form of the invention at least one of the bodies includes an elongate protuberance that removably engages the anchor wire receiving groove, when the pair of concave side edges of the wing are gripped by the holder.

DESCRIPTION OF THE PREFERRED EMBODIMENTS

The holder A as may be seen in FIG. 1 includes a forceps like instrument that includes first and second identical metallic arms 10 and 12 that are resilient, and have end portions 8 bonded together by conventional means (not shown) such as suitable welding or the like. The first and second arms 10 and 12 on the free portions thereof tend to move away from one another.

The first and second arms 10 and 12 have angled extensions 10a and 12a of narrower width that cross over one another and with the free extension end portions 10b, 12b at all times tending to be forced into pressure contact with one another.

First and second identical rigid bodies 14 and 16 are supported from the adjacent side surfaces of the first and second end portions 10b and 12b. The first and second bodies 14 and 16 have convex curved end surfaces 14a and 16a, flat end surfaces 14b, 16b, and pairs of opposed side surfaces 14c and 16c. The first and second end surfaces 14a, 16a have first and second protuberances 14d, 16d extending outwardly from substantially the center thereof. End surfaces 14b and 16b are secured to extensions 10b and 12b by conventional bonding means (not shown) or if desired may be made as an integral part of the extensions.

The holder A may be used in supporting orthodontic brackets C of the type shown in FIGS. 3, 4 and 6 that includes bases 18 that have outwardly extending portions 20 that support wing structures 22 and 23 that have first and second concave end edges 22a and 23a. The base 18 will preferably have a curved rearward surface that substantially conforms to the surface 19 of the tooth D to which the bracket will be bonded.

The end edges 22a and 23a are of the same radii of curvature as the first and second end surfaces 14a and 16a shown in FIG. 3. The wing structure is illustrated in FIGS. 3 to 6 as defined by two laterally spaced portions, but may be a single unit if desired. The wing structures 22 and 23 have an axially aligned anchor wire receiving slots 24 extending there across.

The use and operation of the holder A is extremely simple. Inwardly directed manual forces are applied to the first and second arms 10 and 12 to separate the first and second bodies 14 and 16 to the extent that they are disposed outwardly from the first and second end edges 22a and 23a as shown in FIG. 3. The force on the arms is now relieved for the bodies 14 and 16 to move inwardly towards one another for the first and second end surfaces 14a and 16a to pressure contact the first and second end edges 22a and 23a and frictionally grip the orthodontic bracket C as shown in FIG. 6 to permit it to be moved into a bondable position on the tooth D. When the orthodontic bracket C is so removably gripped the protuberances 14d and 16d will automatically engage the anchor wire receiving grooves 24 to prevent inadvertent rotation of the bracket C relative to the holder A.

A first modified form A-1 of the holder is shown in FIG. 4 that is identical to form A other than the protuberances 14d and 16d are eliminated. Elements of the first modified form A-1 common to form A are identified by the same numerals previously used but with primes added thereto.

A second modified form A-2 of the holder is shown in FIG. 5 in which the extensions 10b and 12b are shaped to define convex end surfaces 30 and 32 that are of the same radii as the concave end edges 22a and 23a. In this form of the invention the use of separate bodies 14 and 16 is eliminated, with the bodies now being an integral part of the extensions 10b and 12b. The second modified form A-2 is used in the same manner as the first modified form A-1.

The use and operation of the orthodontic bracket holder has been described previously in detail and need not be repeated.

What is claimed is:

1. In combination with an orthodontic bracket of the type that includes a base that has a flat rearward surface that may be bonded to a tooth and gingival occlusal wing means disposed outwardly from said base, said wing means defining two spaced end edges of concave arcuate shape that curve inwardly towards one another, the combination with said orthodontic bracket of a holder for removably engaging the same and moving it to a position where said base may be bonded to said tooth, said holder including:
   a. a pair of elongate resilient members that have first and second end portions, said first end portions in abutting bonded engagements, and said second portions defining a pair of interior surfaces that said resilient members tend to maintain in pressure contact; and
   b. a pair of rigid bodies secured to said pair of interior surfaces, said pair of bodies including flat side surfaces and adjacently disposed end surfaces of convex shape that curve away from one another, said pair of elongate members when manipulated to dispose said side surfaces in contact with said base and said end surfaces in pressure contact with said end edges permitting said orthodontic bracket to be moved to a position where it may be bonded to said tooth.

2. A holder as defined in claim 1 in which said wing means defines a transverse anchor wire receiving groove, and in addition:
   c. an elongate protuberance that project from one of said pair of bodies in a direction to removably engage said groove to prevent said pair of bodies inadvertently rotating relative to said wing means when said pair of end surfaces are in pressure gripping contact with said pair of end edges.

3. A holder as defined in claim 1 in which said pair of bodies are an integral part of said elongate members.

4. A holder as defined in claim 2 in which said pair of bodies are an integral part of said elongate members.

* * * * *